United States Patent
Reddi

(10) Patent No.: US 7,976,861 B2
(45) Date of Patent: Jul. 12, 2011

(54) IRRADIATED IMPLANTABLE BONE MATERIAL

(75) Inventor: A. Hari Reddi, El Macero, CA (US)

(73) Assignee: Biomet Manufacturing Corp., Warsaw, IN (US)

(*) Notice: Subject to any disclaimer, the term of this patent is extended or adjusted under 35 U.S.C. 154(b) by 0 days.

(21) Appl. No.: 12/724,123

(22) Filed: Mar. 15, 2010

(65) Prior Publication Data
US 2010/0172954 A1    Jul. 8, 2010

Related U.S. Application Data

(62) Division of application No. 10/834,562, filed on Apr. 28, 2004, now Pat. No. 7,678,385.

(51) Int. Cl.
A61F 2/28 (2006.01)
(52) U.S. Cl. ........ 424/423; 623/23.63; 264/28; 264/488
(58) Field of Classification Search .................. None
See application file for complete search history.

(56) References Cited

U.S. PATENT DOCUMENTS

| | | | |
|---|---|---|---|
| 4,172,128 A | 10/1979 | Thiele et al. | |
| 4,191,747 A | 3/1980 | Scheicher | |
| 4,678,470 A * | 7/1987 | Nashef et al. ............. | 623/23.63 |
| 5,073,373 A | 12/1991 | O'Leary et al. | |
| 5,123,925 A | 6/1992 | Smestad et al. | |
| 5,171,574 A | 12/1992 | Kuberasampath et al. | |
| 5,236,456 A | 8/1993 | O'Leary et al. | |
| 5,290,558 A | 3/1994 | O'Leary et al. | |
| 5,314,476 A | 5/1994 | Prewett et al. | |
| 5,348,788 A | 9/1994 | White | |
| 5,405,390 A | 4/1995 | O'Leary et al. | |
| 5,455,100 A | 10/1995 | White | |
| 5,487,933 A | 1/1996 | White | |
| 5,507,813 A | 4/1996 | Dowd et al. | |
| 5,531,791 A | 7/1996 | Wolfinbarger, Jr. | |
| 5,674,292 A | 10/1997 | Tucker et al. | |
| 5,730,933 A | 3/1998 | Peterson | |
| 5,904,718 A | 5/1999 | Jefferies | |
| 6,013,856 A | 1/2000 | Tucker et al. | |
| 6,123,731 A | 9/2000 | Boyce et al. | |
| 6,180,606 B1 | 1/2001 | Chen et al. | |
| 6,231,608 B1 | 5/2001 | Stone | |
| 6,437,018 B1 | 8/2002 | Gertzman et al. | |
| 6,440,444 B2 | 8/2002 | Boyce et al. | |
| 6,461,630 B1 | 10/2002 | Tucker et al. | |
| 6,504,079 B2 | 1/2003 | Tucker et al. | |
| 6,565,884 B2 | 5/2003 | Nimni | |
| 6,576,249 B1 * | 6/2003 | Gendler et al. ............. | 424/423 |
| 6,679,918 B1 | 1/2004 | Benedict et al. | |
| 7,678,385 B2 * | 3/2010 | Reddi ......................... | 424/423 |
| 2001/0018614 A1 | 8/2001 | Bianchi | |
| 2001/0031254 A1 | 10/2001 | Bianchi et al. | |
| 2003/0074065 A1 | 4/2003 | Stone | |
| 2003/0143258 A1 * | 7/2003 | Knaack et al. ............. | 424/426 |
| 2003/0236573 A1 | 12/2003 | Evans et al. | |
| 2004/0037735 A1 * | 2/2004 | DePaula et al. ............. | 422/20 |
| 2004/0059364 A1 | 3/2004 | Gaskins et al. | |
| 2004/0091459 A1 | 5/2004 | Nimni | |
| 2005/0244450 A1 | 11/2005 | Reddi | |

FOREIGN PATENT DOCUMENTS
WO    WO 03/051240    6/2003

OTHER PUBLICATIONS

Dziedzic-Goclawska et al. "Effect of Radiation Sterilization on the Osteoinductive Properties and the Rate of Remodeling of Bone Implants Preserved by Lyophilization and Deep-Freezing", Clin Orthop Rel Res, 1991, Dec., vol. 272 pp. 30-37.*
Izawa et al., "The effect of heat-treated human bone morphogenetic protein on clinical implantation", Clin Ortho Rel Res 390, 2001, pp. 252-258.
Katz et al., "Radiation-sterilized insoluble collagenous bone matrix is a functional carrier of osteogenin for bone induction", Calcif Tissue Int, 1990, Sep.; 47(3): 183-5.
Leikina et al., "Type I collagen is thermally unstable at body temperature", PNAS, Feb. 5, 2002, vol. 99, No. 3, pp. 1314-1318.
Lewandrowski et al., "An electron microscopic study on the process of acid demineralization of cortical bone", Calcif Tissue Int 61, 1997, pp. 294-297.
Lewandrowski et al., "Improved osteoinduction of cortical bone allografts: a study of the effects of laser perforation and partial demineralization", J Orthop Res 15, 1997, pp. 748-756.
Lewandrowski et al., "Kinetics of cortical bone demineralization: controlled demineralization—a new method for modifying cortical bone allografts", J Biomed Mater Res 31, 1996, pp. 365-372.
Munting et al., "Effect of sterilization on osteoinduction. Comparison of five methods in demineralized rat bone", Acta Orthop Scand, 1988, Feb; 59(1): 34-8.
Reddi et al., "Biochemical sequences in the transformation of normal fibroblasts in adolescent rats", Proc Nat Acad Sci 69, 1972, pp. 1601-1605.
Sato et al., "Heat tolerance of activity toward ectopic bone formation by rabbit bone matrix protein", Ann Chir Gynaecol Suppl 207, 1993, pp. 37-40.
Urist et al., "Exicitation transfer in bone. Deleterious effects of cobalt 60 radiation-sterilization of bank bone", Arch Surg, 1974, Oct.; 109(4): 486-93.
Weintroub et al., "Influence of irradiation on the osteoinductive potential of demineralized bone matrix", Calcif Tissue Int 42, 1988, pp. 255-260.
Mellonig et al., "Tissue Banking and Periodontal Bone Allografts" Committee on Research Science and Therapy, Apr. 1994, pp. 1-6.

* cited by examiner

*Primary Examiner* — Laura Schuberg
(74) *Attorney, Agent, or Firm* — Harness, Dickey

(57) ABSTRACT

A method for making an implantable bone material. The method includes providing a bone composition consisting essentially of demineralized human bone, and irradiating the composition at a temperature less than about 0° C.

4 Claims, No Drawings

IRRADIATED IMPLANTABLE BONE MATERIAL

CROSS-REFERENCE TO RELATED APPLICATION

This application is a divisional application of U.S. patent application Ser. No. 10/834,562 filed Apr. 28, 2004, the entire disclosure of which is incorporated herein by reference.

INTRODUCTION

The present invention relates to compositions and methods for bone repair or growth. In particular, such compositions include those comprising demineralized bone.

Generally, the skeletal structure of mammalian anatomy is strong enough to maintain its rigidity and structure through a given amount of force or use. Nevertheless, the skeletal structure may be weakened or damaged for any of a variety of reasons, including disease, trauma, age, congenital defects, and surgical procedures. A variety of bone repair materials have been described to aid in the repair or reconstruction of such bone defects.

Among the materials that have been suggested for bone repair or reconstruction is bone allograft. One form of bone allograft is demineralized bone, which is typically formed through chemical treatment of bone so as to remove most or all of its mineral content. The remaining demineralized bone matrix ("DBM") consists of the native collagen structure of the bone, along with naturally-occurring growth factors, e.g., bone morphogenetic proteins ("BMPs"). DBM is both osteoinductive and osteoconductive. Osteoconduction is the promotion of differentiated bone-forming cells growth or infiltration into the DBM from the subject in whom the DBM is implanted. Osteoinduction is the promotion of new bone-forming cell production, from non-differentiated cells, in and around the implanted DBM matrix.

DBM is typically provided for clinical use from "bone banks," which harvest bone from human cadavers (donated and managed according to proper ethical and legal standards). The bone undergoes physical processing (such as grinding or shaping), and is then demineralized to form DBM. Because the bone may be harvested and processed in advance of its use, it is frequently dried (e.g., by lyophilization) and packaged under sterile conditions, for storage and shipping to the clinical site.

In practice, however, it has been found that there is significant variability in the bone-building activity of DBM prepared by such techniques. The source of such variability is not understood, but (without limiting the composition, mechanism or utility of the present invention) may be due to differences in the bone taken from source cadavers and variability in the demineralization and other processing of the bone prior to use. In some cases, production lots of DBM are tested to determine their bone building activity (in particular, osteoinductive activity), and samples found to have little or no activity are rejected for use as implant materials.

SUMMARY

The present teachings provide methods of making an implantable bone material. The methods include providing a bone composition consisting essentially of demineralized human bone, and irradiating the composition at a temperature less than about 0° C. The present teachings also provide compositions made by such methods.

The present teachings also provide a method for improving the osteoinductivity of demineralized bone. The method includes providing a bone composition comprising human demineralized bone having little or no osteoinductivity, and irradiating the composition at a temperature less than about 0° C., at a radiation dose sufficient to produce an increase in the osteoinductivity of the composition.

The present teachings also provide a method for producing demineralized bone compositions having uniform baseline osteoinductivity. The method includes obtaining bone portions from a plurality of human donor subjects, demineralizing the bone portions to produce demineralized bone portions, and irradiating the demineralized bone portions at a temperature less than about 0° C.

The present teachings also provide an implantable bone material composition. The composition includes a demineralized bone material, and a pharmaceutically-acceptable carrier. The demineralized bone material is made by a process that includes providing a bone composition consisting essentially of demineralized human bone, and irradiating the composition at a temperature less than about 0° C.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DESCRIPTION

The following definitions and non-limiting guidelines must be considered in reviewing the description of this invention set forth herein.

The headings (such as "Introduction" and "Summary,") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

The present invention provides bone derived compositions for the treatment of bone defects in humans or other animal subjects. Specific materials to be used in the invention must, accordingly, be biocompatible. As used herein, such a "biocompatible" component is one that is suitable for use with humans and/or animals without undue adverse side effects (such as toxicity, irritation, and allergic response) commensurate with a reasonable benefit/risk ratio.

In various embodiments, compositions of the present invention are made by a process comprising:
 (a) providing a bone composition consisting essentially of demineralized human bone; and
 (b) irradiating the composition at a temperature less than about 0° C.

As referred to herein, "demineralized human bone" refers to any human derived bone material which has, in whole or in part, from which a substantial portion of naturally-occurring minerals has been removed. Such bone material includes bone powders and other bone constructs such as cubes, rods, dowels, pins, disks and other formed devices. In one embodiment, the bone construct has been entirely demineralized. In another embodiment, the bone construct has been demineralized in one aspect of its structure, e.g., by demineralizing the surface of the construct. Preferably the mineral content of the demineralized bone is less than about 20%, optionally less than about 10%, optionally from about 0% to about 5%, optionally from about 0% to about 2%, optionally less than about 0.5%. (As referred to herein, all percentages are by weight unless otherwise specified.)

In one embodiment, bone is obtained from animal sources (i.e., for xenogenic implantation in a human subject) such as cows and pigs. In another preferred embodiment, bone is obtained from human cadavers (i.e., for allogenic implantation in a human subject), following appropriate ethical and legal requirements. Such human bone material is available from a variety of tissue banks.

The bone may comprise cortical bone, cancellous bone, or a combination thereof. Cancellous bone is available in a range of porosities based on the location in the body from which the bone is harvested. Highly porous cancellous bone may be harvested from various areas such as the iliac crest, while less porous bone may be harvested from areas such as the tibial condyle femoral head, and calcaneus. Cortical bone may be obtained from long bones, such as the diaphyseal shaft of the femur and tibia. A preferred implant comprises cortical bone.

Depending on the desired end-use of the bone composition, the bone may be subjected to mechanical processing. Such processing may include cutting and shaping, in embodiments forming a construct such as a bone pin or disk for implanting. In one embodiment, the present invention provides a bone powder. In such an embodiment, the bone is preferably initially ground to a selected size. In one embodiment, the bone particulates are less than about 1500 microns in size. In various embodiments, the bone particles range from about 50 microns to about 1000 microns, from about 75 to about 800 microns, or from about 150 to about 600 microns. Depending on the desired composition, particles may be of a variety of sizes.

The bone is demineralized using any of a variety of methods, including those known in the art using acids, chelating agents and electrolysis. Preferred chemical treatments include those using hydrochloric acid, ethylene diamine tetraacetic acid (EDTA), peracetic acid, or citric acid. Demineralization techniques among those useful herein are described in K. U. Lewandrowski et al., "Kinetics of cortical bone demineralization: controlled demineralization—a new method for modifying cortical bone allografts," *J Biomed. Mater. Res.*, 31:365-372 (1996); K. U. Lewandrowski, et al., "An electron microscopic study on the process of acid demineralization of cortical bone," *Cal. Tiss. Int.*, 61:294-297 (1997); and K. U. Lewandrowski, et al., "Improved osteoinduction of cortical bone allografts: a study of the effects of laser perforation and partial demineralization," *J Orthop. Res.*, 15:748-756 (1997); and Reddi et al., "Biochemical sequences in the transformation of normal fibroblasts in adolescent rats", Proc. Nat. Acad. Sci., 69 pp. 1601-5 (1972).

The demineralization treatment provides a DBM comprising insoluble collagen and other non-collagenous proteins such as bone growth factors including bone morphogenetic proteins (BMPs). The methods of this invention comprise the irradiation of bone material consisting essentially of DBM. Such compositions comprise DBM that has not undergone treatments that destroy the chemical composition of collagen, or denature bone growth factors within the DBM. Such DBM to be irradiated does not comprise added osteogenic proteins. As referred to herein, "osteogenic proteins" are proteins that are capable of producing a developmental cascade of cellular events resulting in endochondral bone function. Such osteogenic proteins are those referred to in the art as osteogenic proteins, osteoinductive proteins and bone morphogenetic proteins. The DBM may, however, include non-osteogenic proteins and active materials, such as those selected from the group consisting of synthetic and recombinant growth factors, growth factor mimetics, morphogens, and plasmid and viral vectors. Products made using such compositions may further comprise added osteogenic proteins and such non-osteogenic proteins and active materials added to the irradiated DBM after irradiation.

In one embodiment, the bone is subjected to defatting/disinfecting and acid demineralization treatments. A preferred defatting/disinfectant solution is an aqueous solution of a lower alcohol, such as ethanol. Preferably, the defatting/disinfection solution contains at least about 10% to 40% water (i.e., about 60% to 90% defatting agent such as alcohol). Preferably, the solution contains from about 60% to about 85% alcohol. Following defatting, the bone is immersed in acid or chelating agent over time to effect demineralization. The concentration of the acid or chelating agent in such demineralization operation is preferably about 0.5N to about 1.0N, with demineralizing time being from about 2 to about 12 hours under ambient conditions.

The methods of the present invention comprise irradiating the demineralized bone at a temperature less than about 0° C. Such irradiation methods include ionizing radiation, such as electron beam radiation and gamma radiation. In a preferred embodiment, DBM is irradiated with gamma irradiation. In various embodiments, the dosage of radiation is from about 0.5 to about 15 megarads (Mrad), from about 1 to about 10 Mrad, from about 1.5 to about 5 Mrad, from about 2 to about 5 Mrad, from about 2 to about 4 Mrad, or from about 2 to about 3.5 Mrad.

The irradiation may be performed at any point in the process after formation of the DBM, and may be performed one or more times during the process. In one embodiment, irradiation is performed prior to preparation of the final product form. In another embodiment, irradiation is performed after preparation of the final product form, preferably at a level which is sufficient to effect sterilization of the product form. Radiation dosages required for obtaining a sterility assurance level for a particular device can be determined from the "Association for the Advancement of Medical Instrumentation Guidelines" published in 1992.

Irradiation is performed at a temperature less than about 0° C. In one embodiment, irradiation is performed at a temperature of from about −15° C. to about −25° C. In one embodiment, the DBM is cooled using dry ice.

In various embodiments, the present invention provides bone materials formed from DBM that is prepared and treated to induce and/or increase bone growth activity in the subject to whom the DBM is implanted. Such bone growth activity includes osteoinduction. In one embodiment, the osteoinductivity of a given human DBM composition is increased. In one embodiment, the present invention provides a method for improving the osteoinductivity of demineralized bone, comprising:
(a) providing a bone composition comprising human demineralized bone having little or no osteoinductivity; and
(b) irradiating the composition at a temperature less than about 0° C., at a radiation dose sufficient to produce an increase in the osteoinductivity of the composition.

In one embodiment, the present invention provides methods for producing demineralized bone compositions having uniform osteoinductivity, the method comprising:
(a) obtaining bone portions from a plurality of human donor subjects;
(b) demineralizing the bone portions to produce demineralized bone portions; and
(c) irradiating the demineralized bone portions at a temperature less than about 0° C.

In such methods, DBM portions from different human donors that have different levels of osteoinductivity, including little or no osteoinductivity, can be normalized by irradiating as above, such that all the DBM portions have a non-zero baseline level of osteoinductivity when implanted. Moreover, the level of osteoinductivity can have a desirable distribution among portions and can be also made to be substantially uniform among portions.

In various embodiments, osteoinductive activity is determined using an accepted in vivo or in vitro measurement of activity. Such methods include in vivo implantation methods with histological analysis, and in vitro assays such as alkaline phosphatase assays and cell proliferation assays. In one embodiment, comprising obtaining bone portions from a plurality of human donor subjects, samples of the portions are tested before and after irradiation. In a preferred embodiment, no such testing is performed.

A suitable test comprises a rat in vivo model. In one such model, approximate 0.3 cc aliquots of the compositions are aseptically packed into 1 cc syringes with the barrel blunt cut at a 45° angle. Male rats (strain Hsd: Rh-rnu) are weighed and randomly assigned to a treatment group. The material is placed in a pocket created between the semi-membranous and adductor muscle group in close proximity to the femur. The material is implanted in each leg. Body weights are recorded prior to implantation, weekly and at termination. Animals are observed daily for general health and detailed examinations for clinical signs of disease or abnormality are conducted at randomization, weekly and at termination. After 28 days, the rats are euthanized and the entire limbs are removed and fixed. The entire implant area, including the femur, is transected above and below the implant area. The harvested tissues are sectioned at multiple levels (proximal, middle and distal implant area), decalcified overnight and histologically processed (embedded, sectioned and stained in hematoxylin and eosin and Toluidine blue).

Following processing, all tissue sections are examined for new bone and new cartilage and evaluated with a microscopic scoring scheme based on the following Osteoinduction Grading Scale:
0=0% of implant area occupied by new bone
1=1-25% endochondral ossification and/or new bone covering 1-25% of implant
2=26-50% endochondral ossification and/or new bone covering 26-50% of implant
3=51-75% endochondral ossification and/or new bone covering 51-75% of implant
4=76-100% endochondral ossification and/or new bone covering 76-100% of implant.

In another embodiment, the tissue sections are evaluated according to the following Modified Schwartz System:
0=no implant
1=implant present, no new bone or cartilage present
2=<25% endochondral ossification and/or new bone covering <25% of implant
26-50% endochondral ossification and/or new bone covering 26-50% of implant
4=>50% endochondral ossification and/or new bone covering >50% of implant Irradiating human donor DBM with a selected dose of radiation as described above, assures that the radiation-treated DBM will have a known baseline level of osteoinductivity regardless of whether the DBM is osteoinductive or not before irradiation. For example, three batches of DBM having osteoinductivity grade scores of 0, 1 and 3, respectively, are irradiated with a dose of 2.5 Mrad. The irradiated batches will have at least an osteoinductive grade score of 2. Therefore, the baseline level of osteoinductivity is uniformly raised to 2, meaning that no batch has osteoinductivity grade score less that 2.

The processes of the present invention optionally comprise other steps, including physical processing of the DBM, sterilization, and packaging. Such additional process steps may be performed before or after irradiation. The demineralization process may produce a particulate or other product, which may be further ground to a substantially fine particulate in the form of DBM powder. It will be understood that the DBM powder may be formed in any appropriate manner as required in a particular clinical application or procedure. Sterilization includes irradiation, as described above, or chemical sterilization techniques (such as using ethylene oxide). Packaging includes methods suitable for convenient storage, handling or transport of the composition after preparation and before use. In one embodiment, such packaging includes lyophilization of the composition to remove substantially all water.

The radiation-treated DBM powder made thereof may be further enhanced for osteoinduction by heat treatment, as disclosed in co-filed U.S. patent application Ser. No. 10/835,519, Reddi, "Heat-Treated Implantable Bone Material Introduction", incorporated herein by reference. The heat treatment process includes forming a mixture of DBM powder and water, and heating the mixture under non-denaturing conditions, preferably effective to melt or otherwise alter the collagen that is native to the DBM. The phrase "non-denaturing conditions effective to physically alter the collagen" is understood to mean temperature and pressure conditions effective to change the physical structure of the collagen in the DBM without significantly altering the chemical composition of the individual stands of the collagen structure. Under these conditions, heating is, for example, below the temperature that converts collagen into gelatin at a given pressure.

The compositions of the present invention may be used in any of a variety of clinical procedures for the treatment of bone defects. As referred to herein such "bone defects" include any condition involving skeletal tissue which is inadequate for physiological or cosmetic purposes. Such defects include those that are congenital, the result of disease or trauma, and consequent to surgical or other medical procedures. Specific defects include those resulting from bone fractures, osteoporosis, spinal fixation procedures, and hip and other joint replacement procedures. The DBM composition may be used to assist in bone reconstruction, soft tissue fixation and the like, either as-is, as a wet or dry or lyophilized DBM powder, or formulated into putty, sheet, or other DBM product. In various embodiments, the composition is combined with another material, composition, or device. Suitable products comprising a composition of the present invention include those disclosed in U.S. Pat. No. 5,348,788, White, issued Sep. 20, 1994; U.S. Pat. No. 5,455,100, White, issued Oct. 3, 1995; and U.S. Pat. No. 5,487,933, White, issued Jan. 30, 1996; U.S. Pat. No. 6,576,249, Gendler et al., issued Jun. 10, 2003; and PCT Patent Publication .WO 03/051240, Schwardt et al, published Jun. 26, 2003.

In one embodiment, a composition of invention is formed into a product/article or into a particular shape, either with the use of a carrier, or a binder, or simply by shaping the powder into a selected shape in a pocket, recess, bore or other receiving surface of the implantation site. The article or shape could be a sheet, a disc or other flat plate, an elongated member, such as a bar or rod, a bone-shaped member, or any other member shaped to be received in a bore of a bone or other body portion, including a plug, a ball or other article shaped for filling a cavity of the same shape. The article can also be a two- or three-dimensional porous structure with holes or depressions and protrusions, which can be formed by using appropriate mesh sheets as discussed above.

The composition of the invention may also be mixed with a biocompatible carrier. Such carriers include saline, hyaluronic acid, cellulose ethers (such as carboxymethyl cellulose), collagen, gelatin, autoclaved bone powder, osteoconductive carriers, and mixtures thereof. Osteoinductive carriers include allograft bone particles, other demineralized bone matrix, calcium phosphate, calcium sulfate, hydroxyapatite, polylactic acid, polyglycolic acid and mixtures thereof. Other carriers include blood, monosaccharides, disaccharides, water dispersible oligosaccharides, polysaccharides, low weight organic solvents, including glycerol, polyhydroxy compounds, such as mucopolysaccharide or polyhyaluronic acid and various aqueous solutions, as described in U.S. Pat. Nos. 5,290,558; 5,073,373; 5,314,476; 5,507,813; 4,172,128; and 4,191,747. In one embodiment, the carrier comprises gelatin. In one embodiment, the carrier is a bone-derived material. One such bone-derived material is made by mixing DBM with water or saline, and heating under denaturing conditions to form a viscous composition. Preferably, the DBM mixture is heated under autoclaving conditions, at a temperature of at least about 85° C. and pressure of at least about 15 psi, for at least about 1 hour. Optionally, the autoclaving is at a temperature of from about 85° C. to about 100° C. and a pressure of from about 15 psi to about 90 psi, for from about 1 to about 8 hours. Such compositions are described in U.S. Pat. No. 6,576,249, Gendler et al., issued Jun. 10, 2003.

In one embodiment, the composition is positioned in a selected position or orientation for implantation, which includes a predefined shape. For example, the radiation-treated DBM powder may be positioned in a bore, either with or without a binder or adhesive, such as bone cement, and the bore may form the shape which the DBM powder will take, such that the DBM powder is not preformed in a selected shape. Therefore, forming the DBM powder into a selected shape before implantation will be understood to be optional and not necessary.

The present invention is further illustrated through the following non-limiting example.

EXAMPLE

In a method of this invention, bone is harvested from a single human donor. The bone is ground to and fractionated to have a particle size of from about 150 to 600 microns. The powder is lipid extracted in ethanol, and demineralized with 0.6N HCl for about 12 hours. The DBM powder is frozen to −20° C. and packaged on dry ice. Samples of the frozen DBM are irradiated with gamma radiation of doses 0, 1 Mrad, 2.5 Mrad and 5 Mrad.

The osteoinductivity of the samples is then tested using the rat osteoinduction model described above. The donor DBM has no detectable osteoinductivity, evidenced by the fact that the non-irradiated implants produce a zero grade score. Implants irradiated with 1 Mrad radiation dose produce a grade score of 1. Implants irradiated with 2 Mrad radiation dose produce a grade score of 2, and implants irradiated with 5 Mrad radiation dose produce a grade score of 2.5.

Further to the above example, samples of the composition that were indicated at 5 Mrad are lyophilized. A sample is then mixed with blood obtained from a human subject undergoing a hip replacement procedure to form a material having a putty-like consistency. The material is then implanted at the surgical site to fill voids around the site of the implant. Radiographic images of the surgical site one month after surgery reveal significant bone building at the site of the implant.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. A method for producing demineralized bone compositions having uniform osteoinductivity, the method comprising:
   (a) obtaining bone portions from a human donor subject;
   (b) demineralizing the bone portions to produce demineralized bone portions having no osteoinductivity; and
   (c) irradiating the demineralized bone portions at a temperature less than about 0° C. and at a dose of radiation sufficient to increase osteoinductivity to an Osteoinduction Grading Score of at least 2.

2. A method according to claim 1, wherein the bone portions are obtained from a plurality of donor subjects.

3. A method according to claim 1, wherein the demineralized bone portions comprise bone powder.

4. A method according to claim 1, wherein irradiating comprises administering a sterilizing dose of radiation.

* * * * *

UNITED STATES PATENT AND TRADEMARK OFFICE
CERTIFICATE OF CORRECTION

PATENT NO.       : 7,976,861 B2
APPLICATION NO.  : 12/724123
DATED            : July 12, 2011
INVENTOR(S)      : Reddi It is certified that error appears in the above-identified patent and that said Letters Patent is hereby corrected as shown below:

Col. 6, line 23: "26-50%" should be -- 3 = 26-50% --

Signed and Sealed this
Seventeenth Day of January, 2012

David J. Kappos
*Director of the United States Patent and Trademark Office*